United States Patent
Kaethner et al.

(10) Patent No.: US 12,161,431 B2
(45) Date of Patent: Dec. 10, 2024

(54) MONITORING METHOD AND MEDICAL SYSTEM

(71) Applicant: Siemens Healthcare GmbH, Erlangen (DE)

(72) Inventors: Christian Kaethner, Forchheim (DE); Andreas Meyer, Bubenreuth (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 266 days.

(21) Appl. No.: 17/244,922

(22) Filed: Apr. 29, 2021

(65) Prior Publication Data
US 2021/0338346 A1 Nov. 4, 2021

(30) Foreign Application Priority Data
Apr. 30, 2020 (DE) .................... 10 2020 205 546.7

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *A61B 90/37* (2016.02);
(Continued)

(58) Field of Classification Search
CPC .... A61B 17/00234; A61B 2017/00323; A61B 2017/00477; A61B 34/30; A61B 2034/301
See application file for complete search history.

(56) References Cited

U.S. PATENT DOCUMENTS

2002/0077546 A1 6/2002 Aldefeld
2004/0097805 A1 5/2004 Verard
(Continued)

FOREIGN PATENT DOCUMENTS

CN 103654813 A 3/2014
CN 105578985 A 5/2016
(Continued)

OTHER PUBLICATIONS

German Office Action for German Application No. 10 2020 205 546.7 dated Feb. 19, 2021.

*Primary Examiner* — Boniface N Nganga
(74) *Attorney, Agent, or Firm* — Lempia Summerfield Katz LLC

(57) ABSTRACT

A method for automatically monitoring a robot-assisted movement of a medical object through a hollow organ of a medical object of a patient performed by a robotic system is provided. The method includes tracking movement of the medical object using a medical imaging device such that the medical object and/or the hollow organ is at least partially arranged in a recording region that is mappable by the imaging device. The tracking is effected by a relative movement between the recording system of the imaging device and the patient. An image of the recording region is recorded during the tracking. In each case, a further image is recorded at regular intervals. The current image in each case and/or sensor data from a sensor assigned to the robotic system or the object is evaluated to determine whether a situation relevant to decision-making and/or safety with respect to the robotic system is present.

13 Claims, 4 Drawing Sheets

(51) Int. Cl.
    *A61B 34/32*     (2016.01)
    *A61B 90/00*     (2016.01)

(52) U.S. Cl.
    CPC . *A61B 2034/2065* (2016.02); *A61B 2034/301* (2016.02); *A61B 2090/3764* (2016.02)

(56) References Cited

U.S. PATENT DOCUMENTS

| | | |
|---|---|---|
| 2005/0054910 A1 | 3/2005 | Tremblay |
| 2010/0069833 A1 | 3/2010 | Wenderow et al. |
| 2012/0143045 A1* | 6/2012 | Klingenbeck ......... A61B 5/062 |
| | | 600/424 |
| 2012/0165652 A1 | 6/2012 | Dempsey |
| 2012/0289783 A1 | 11/2012 | Duindam et al. |
| 2013/0231678 A1* | 9/2013 | Wenderow ............ A61B 34/30 |
| | | 606/130 |
| 2016/0278731 A1 | 9/2016 | Babic |
| 2019/0046275 A1 | 2/2019 | Winneberger |
| 2019/0050984 A1 | 2/2019 | Blendinger |
| 2019/0261932 A1 | 8/2019 | Divoky |
| 2020/0093456 A1 | 3/2020 | Fischer et al. |

FOREIGN PATENT DOCUMENTS

| | | | | |
|---|---|---|---|---|
| CN | 109890295 A | 6/2019 | | |
| CN | 110946600 A | 4/2020 | | |
| CN | 109389620 B | 2/2023 | | |
| DE | 102005028744 A1 * | 12/2006 | ............. | A61B 34/20 |
| EP | 2654574 B1 | 5/2017 | | |
| EP | 3406291 B1 | 12/2019 | | |
| WO | 2012158325 A3 | 1/2013 | | |
| WO | WO-2016116821 A1 * | 7/2016 | ............. | A61B 34/20 |
| WO | WO-2018195216 A1 * | 10/2018 | ............. | A61B 34/10 |

* cited by examiner

MONITORING METHOD AND MEDICAL SYSTEM

This application claims the benefit of German Patent Application No. DE 10 2020 205 546.7, filed on Apr. 30, 2020, which is hereby incorporated by reference in its entirety.

BACKGROUND

The present embodiments relate to automatically monitoring a robot-assisted movement of a medical object.

Interventional medical procedures in hollow organs (e.g., the vascular system of the human body) require medical objects (e.g., devices or instruments) to be introduced into the vascular system via a percutaneous vascular access and to be guided to the target region to be treated. Conventionally, the practitioner introduces the objects (e.g., guiding catheters, microcatheters, or guide wires) into the vascular system via a sheath under X-ray fluoroscopy and then navigates the object into the target region with the aid of contrast medium injections in order to visualize the vessels. Herein, in many cases, the practitioner, together with an assistant, stands right next to the patient table in order to perform the procedure.

A further development of this medical approach interposes a robotic system between the hands of the practitioner and the patient with the advantage that the practitioner no longer has to stand directly at the mounting table for the patient but is able to maneuver the objects (e.g., rotational, forward and backward movement) remotely. In principle, robotic systems are known by which a robot-assisted semi-automatic or automatic advance of an object (e.g., a catheter and/or guide wire) may be effected in a cavity organ of a patient (e.g., from EP 3406291 B1). For this, the practitioner is provided with a corresponding user interface for the remote-controlled movements. For the necessary visual feedback, it is also advantageous to record fluoroscopic images of an X-ray system, transmit the recorded fluoroscopic images, and display the recorded fluoroscopic images to the practitioner. The advantage of this robotic guidance of the medical object includes the comfortable working position of the practitioner, the possibility of being able to leave the region of radiation at the patient table entirely, and thus, increased occupational safety through avoidance of radiation.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that enables a procedure to be further automated and a suitable medical system for performing the method are provided.

A method according to the present embodiments for automatically monitoring a robot-assisted movement of a medical object (e.g., an instrument) through a hollow organ of a patient performed by a robotic system includes tracking the movement of the medical object by a medical imaging device such that the medical object and/or the hollow organ are at least partially arranged in the recording region that may be mapped by the imaging device. The tracking is effected by a relative movement between the recording system of the imaging device and the patient. The method also includes recording at least one image of the recording region during the tracking. In each case, a further image is recorded at regular intervals. The method includes evaluating the current image in each case and/or sensor data from a sensor assigned to the robotic system or the object to determine whether a situation relevant to decision-making and/or safety with respect to the robotic system is present. The method also includes outputting information if the evaluation reveals the presence of a situation relevant to decision-making and/or safety.

In principle, robotic systems are known by which a robot-assisted automatic (e.g., semi-automatic) advance of an object (e.g., a catheter and/or guidewire) may be effected in a cavity organ of a patient (e.g., from EP 3406291 B1). For this, the practitioner is provided with a corresponding user interface for the remote-controlled movements. The method according to the present embodiments enables further automation by additional automatic monitoring so that, in addition to improved safety with the known semi-automatic method, the advance may also, for example, be effected fully automatically based on path planning. Patient safety is also further improved with such a method, since automatic seamless monitoring of the advance movements is provided, and it is possible to react to critical situations or abort criteria immediately. Overall, a medical imaging device (e.g., an X-ray device) follows the advance of the object so that the object is always arranged in the recording region of the imaging device. This provides advantageous synchronization with the imaging device. The tracking may be performed either by a movement of the recording system of the imaging device or by a movement of the patient table/the table top of the patient table, on which the patient is mounted or by a joint movement of the recording system and patient table relative to one another.

During the tracking, a further current image is recorded and evaluated regularly (e.g., by image recognition and/or image processing algorithms and/or by pretrained machine-learning algorithms). The evaluation is performed to determine whether a situation relevant to decision-making and/or safety is present and, if this is the case, information is output. The information may be output in different ways (e.g., by displaying an image, displaying optical signals, or outputting acoustic or haptic warnings). An operator may thereby be made aware that action or intervention is required. In addition to an evaluation of the images of the imaging device, it is also possible to use additional information from sensors and other apparatuses to indicate situations relevant to decision-making and/or safety (e.g., navigation devices, cameras, or sensors arranged on the object).

According to one embodiment, in addition to an information display (e.g., on a screen), a control signal for interrupting the robot-assisted movement and/or the image recording is automatically output if the evaluation reveals the presence of a situation relevant to decision-making and/or safety. An interruption of this kind is a safety measure to prevent a further advance of the object causing a path deviation or even injury or damage to the hollow organ. This protects the patient and provides optimal performance of an examination.

According to a further embodiment, the current image, the evaluation of which reveals the presence of a situation relevant to decision-making and/or safety and/or the current image that was recorded at the same point in time as the sensor data that reveals the presence of a situation relevant to decision-making and/or safety, is displayed, for example, until acceptance of a user input or until receipt of a control command for resuming the robot-assisted movement and/or the image recording. This is a last image hold (LIH) with which the critical image is displayed permanently in order to give the operator the opportunity to examine the critical situation in detail and, if necessary, initiate measures to resolve the situation (e.g., to withdraw the object for a part of the path, to follow a certain branch of the hollow organ, to slow the movement, to initiate contrast medium administration, etc.). After resolving the situation, the operator may then, for example, decide to resume the robot-assisted movement and thus also to resume the method according to the present embodiments.

According to a further embodiment, the tracking takes place at least partially based on control signals from the robotic system. The control signals may be transferred to the imaging device in order to give its system control the opportunity of improving the corresponding following movement of the recording system or of the patient table and making the movement even more precise.

In one embodiment, a situation relevant to decision-making and/or safety is present if a branch, a bifurcation, a peculiarity, or another anomaly of the hollow organ is detected during the evaluation (e.g., of the respective image or sensor signal) or if a deviation from existing path planning of the object exceeds a predefined or preset threshold value, for example.

According to a further embodiment, path planning for an automatic or semi-automatic movement of the medical object is provided. This may, for example, also be used to simplify the tracking of the imaging device and to decide whether a situation relevant to decision-making and/or safety is present.

The present embodiments may also include a medical system for performing a method as described above having a robotic system with at least one robot control unit and one robot-assisted drive system with a drive and a drive mechanism. The drive system is configured to move a medical object in a cavity organ of a patient based on control signals from the robot control unit. The medical system also includes an imaging device with a system control unit and a movable recording system for recording images of a mappable recording region. The system control is configured to actuate the recording system for tracking the movement of the medical object. The medical system also includes an evaluation unit for evaluating images of the recording system to determine whether a situation relevant to decision-making and/or safety with respect to the robotic system is present. The medical system includes an output unit for outputting information. In one embodiment, the output unit is formed by a display unit. The medical system may also include an input unit for the actuation of the robotic system by an operator.

In one embodiment, for improved tracking of the object by the imaging device, the robot control unit and the system control unit are configured to exchange data.

According to one embodiment, the medical system has a patient table with a table top, where the patient table and/or the table top may be actuated to execute a movement relative to the recording system. In this way, the tracking may also or exclusively be performed by a movement of the patient table/the table top (e.g., of the patient) relative to the recording system. This may, for example, entail translational movements or tilting.

According to a further embodiment of the present embodiments, the medical system has a position-determining system with at least one sensor. The sensor is arranged on or assigned to the robotic system or the object. The position-determining system is configured to determine a position of the object. The position-determining system sends the position information to the imaging device in order to facilitate the tracking and to be able to better evaluate situations relevant to decision-making and/or safety.

DETAILED DESCRIPTION

Figure 1:
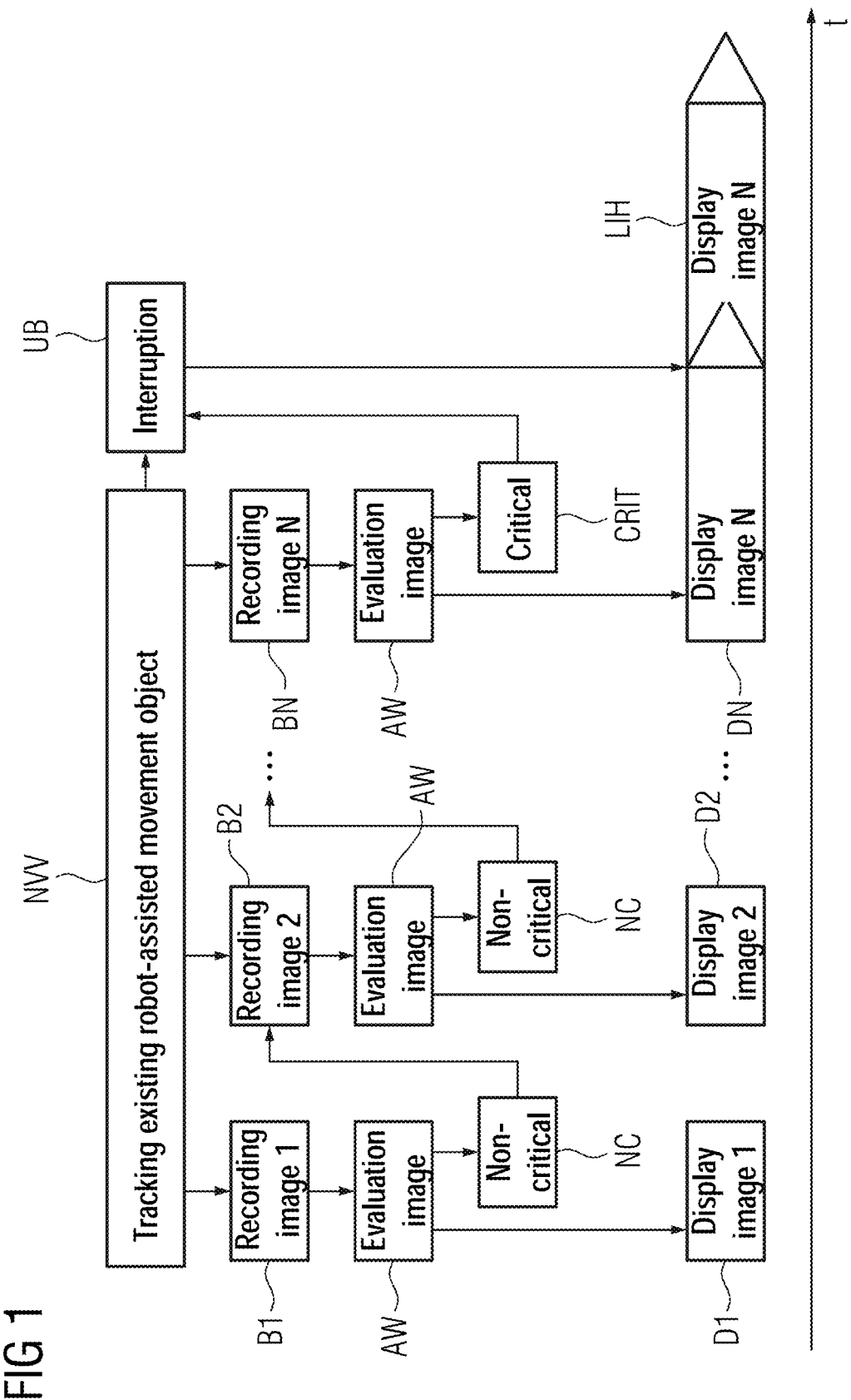
FIG. 1 shows a sequence of acts of one embodiment of a method.
Figure 2:
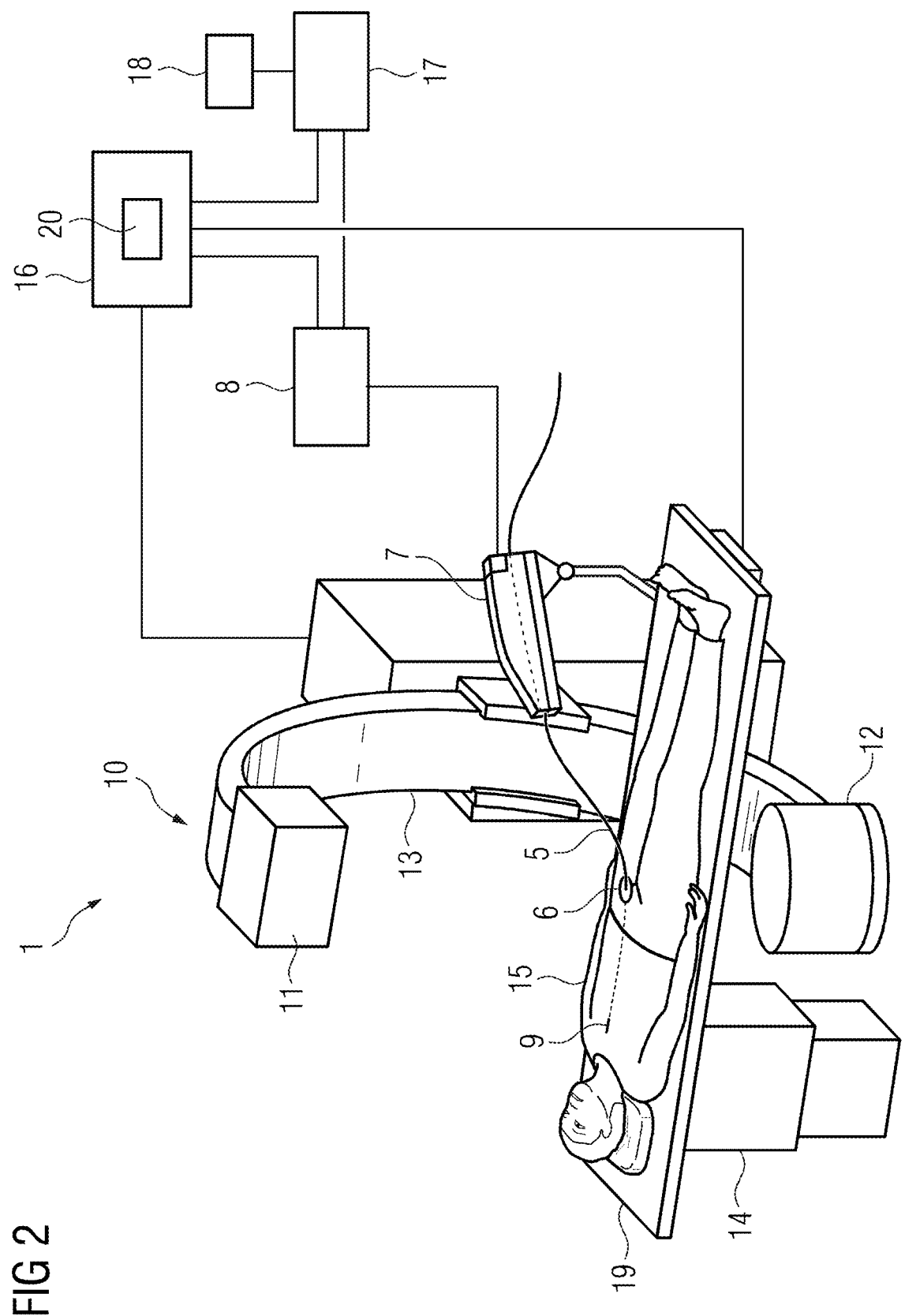
FIG. 2 shows a view of one embodiment of a medical system.

FIG. 1 shows acts of a method for automatically monitoring a robot-assisted movement of a medical object through a hollow organ of a patient performed by a robotic system. FIG. 2 shows a medical system 1 embodied to perform the method.

The medical system 1 has a robotic system and an imaging device (e.g., an X-ray device 10). The robotic system is configured to semi-automatically or automatically advance at least one object (e.g., an instrument, stent, guide wire 5, or catheter) in a hollow organ of a patient 15. Herein, semi-automatic actuation may, for example, be actuation that may be transmitted by an operator via an input unit 17 (e.g., a joystick, touchpad, rotary regulator, etc.) to a robot control unit 8. The robotic system has at least one robot control unit 8 and one robot-assisted drive system 7. The drive system 7 is configured to move the medical object (e.g., a guide wire 5) in a cavity organ of a patient 15 after the medical object has been introduced at an entry point 6 based on control signals from the robot control unit 8. Herein, the drive system 7 includes at least one drive and one drive mechanism (not shown; for example, known from EP 3406291 B1). The drive mechanism is detachably coupled to the guide wire 5, for example. The drive mechanism and the drive may be used to axially advance and withdraw the guide wire 5 and/or additionally move the guide wire 5 rotationally. The robot control unit 8 is connected to an input unit 17 (e.g., remote from the patient), which may be operated by an operator (e.g., a surgeon). The control signals are transmitted from the input unit 17 (e.g., one or more joysticks, touchpads, control buttons, etc.) to the robot control unit 8, and in this way, the movements of the object are actuated semi-automatically. Alternatively, the operator may plan a path for the object or have the path created automatically. This is transmitted to the robot control unit 8, thus enabling a fully automatic movement to take place. The path planning may also be used as a reference for a semi-automatic movement.

To obtain an overview of the intervention and the movement, the imaging device (e.g., an X-ray device 10) is provided. The X-ray device 10 has, for example, a C-arm 13 that holds an X-ray source 12 and an X-ray detector 11 and is connected to a system control 16. The C-arm 13 is arranged movably relative to the patient; in the case of a mobile X-ray device, it is also possible for the entire X-ray device to be moved. Alternatively or additionally, it is also possible for the patient table 14 or only the top 19 of the patient table 14 to be moved relative to the X-ray device or recording system. The X-ray device 10 enables images of a mappable recording region to be created and displayed on a display unit 18. The robot control unit 8 and the system control 16 of the imaging device enables data items to be exchanged bidirectionally and to communicate with each other. It is also possible for a common control including the robot control unit 8 and the system control 16 to be provided.

Figure 4:
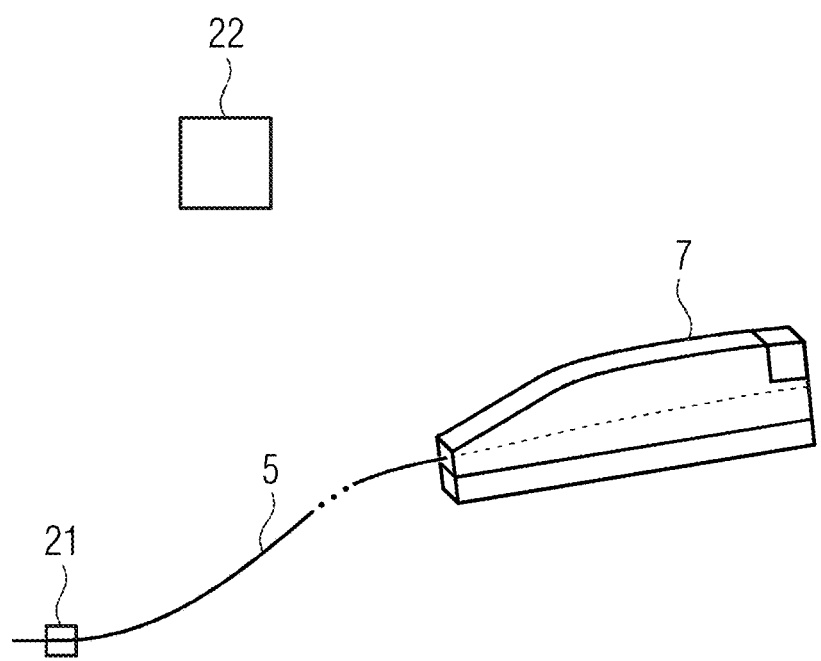
FIG. 4 shows a view of one embodiment of a position-determining system with a sensor arranged on the object.

In the context of the method according to the present embodiments, the movements of the object are tracked NVV by the imaging. To enable the movements of the object through the hollow organ to be observed, it is important that the object and/or the hollow organ are always arranged at least partially in the recording region of the recording system of the imaging device. This may, for example, take place by way of a movement of the recording system along the path of the object and/or a movement of the patient table 14 relative to the recording system. The movements are actuatable by the system control of the X-ray device. There are various possibilities for accomplishing such tracking. For example, control signals from the robotic system may be forwarded from the robot control unit 8 to the system control 16 and used for, or at least included in, the tracking. It is also possible for path planning that has already been created to be used to control or optimize the tracking. It is also possible for additional position-determining systems to be used to determine the position of the object and used for the tracking. A position-determining system may determine the precise position of the object (e.g., using at least one sensor, such as a position sensor 21, see FIG. 4, on the object and an associated readout unit 22).

During the tracking NVV, at least one first image (e.g., a fluoroscopy image) of the recording region is recorded B1, where in each case a further image is recorded (B2 . . . BN) continuously or at regular intervals and, for example, also displayed on the display unit 18. The display unit 18 in each case displays the current image so that the operator is given an overview of the advance of the object. As soon as the first image has been recorded B1, the first image is displayed D1. When the second image has been recorded B2, the second image is displayed D2, etc. The image recorded in each case is also evaluated AW directly online to determine whether a situation relevant to decision-making and/or safety with respect to the robotic system is present. For this evaluation AW, the image is analyzed (e.g., with the aid of an image recognition system) to determine whether a branch, a bifurcation, a peculiarity, or an anomaly of the hollow organ is present. It is also possible for an analysis to be performed to determine whether a deviation of the path of the object from an existing path planning exceeds a certain (e.g., preset) threshold value and/or whether any other error tolerance is exceeded. In the case of the evaluation AW with respect to a situation relevant to decision-making and/or safety, as well as the images, it is also possible to include further data (e.g., from a position-determining system or another measuring system or sensor).

If the evaluation reveals a non-critical situation NC, the method is continued in that the tracking NVV and the recording Bk, display Dk, and evaluation AW of further images takes place (where k=1, 2, . . . , N).

Figure 3:
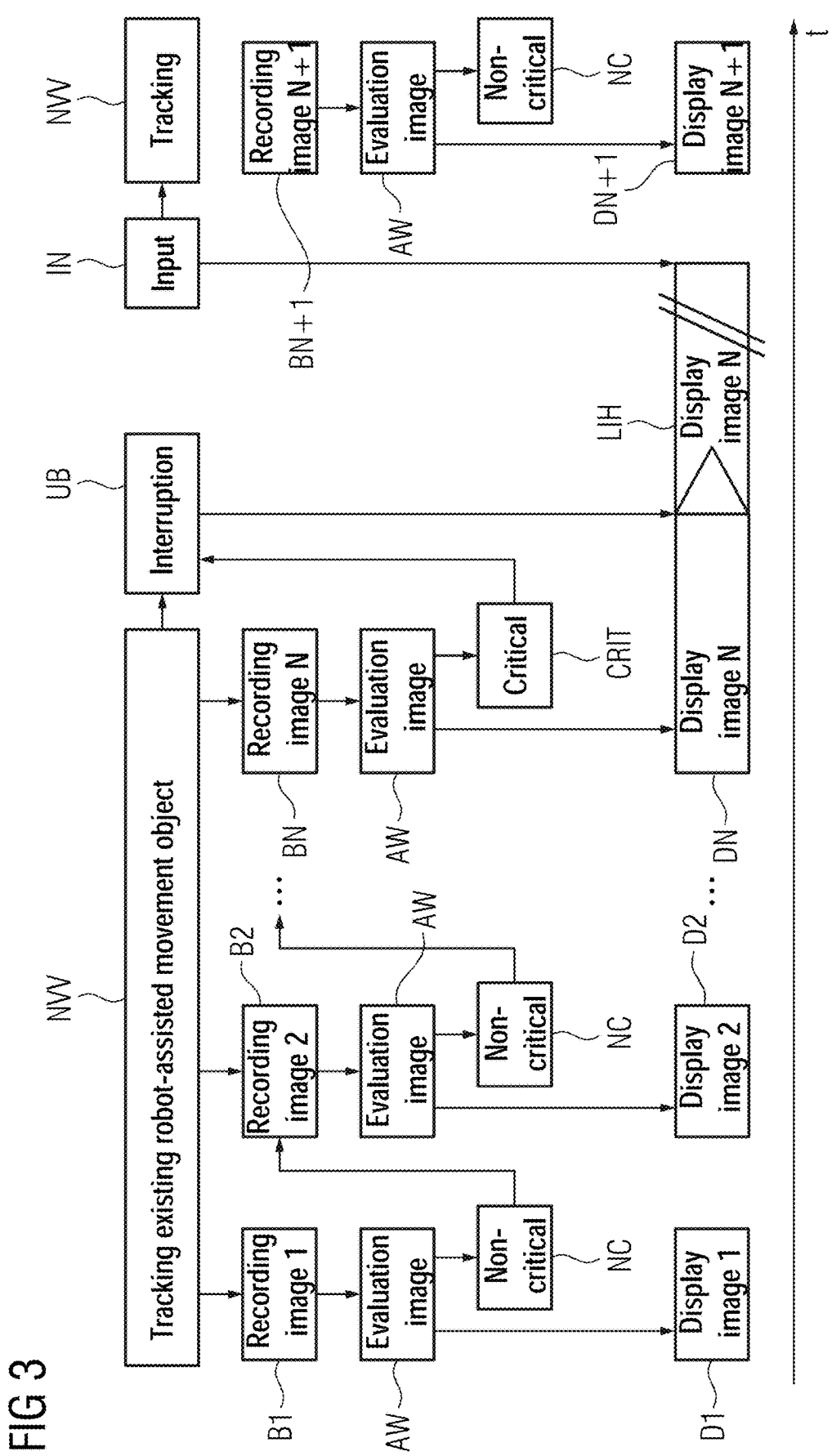
FIG. 3 shows a further sequence of acts of a method according to FIG. 1.

If, after the recording BN of the Nth image, the evaluation reveals a situation relevant to decision-making and/or safety CRIT for this image, a control signal for aborting or interrupting UB the robot-assisted movement and the image recording is automatically output immediately. At the same time, the display DN of the Nth image is extended LIH until, for example, the acceptance of a user input IN to terminate the display or resume the method or until receipt of a control command to resume the robot-assisted movement and/or the image recording (see, e.g., FIG. 3). Therefore, a last image hold LIH takes place so that the critical Nth image remains visible to an operator until revoked. The last image hold LIH in each case takes place with the current image, the evaluation of which has revealed a critical situation or which has just been recorded or displayed (e.g., a critical situation was detected). In this way, the operator may appraise and analyze the critical situation in detail while the movements are not continued. This enables the operator to initiate measures to resolve the situation if necessary or simply to cancel the interruption UB of the robot-assisted movement and/or the method (e.g., by an input IN).

Also, it is possible for further signals to be output together with the interruption, such as, for example, optical, acoustic, or haptic warning signals. It is also possible for prompts or suggestions for certain actions to be output and displayed to the operator (e.g., a suggestion for contrast medium administration (when the situation relevant to decision-making and/or safety consisted in that the hollow organ was no longer recognizable on the image), a suggestion for path correction (when a threshold value for a path deviation from a planned path is exceeded), a suggestion for a branch (in the case of a bifurcation), or a suggestion that the movement be slowed down).

Optical, acoustic, or haptic signals may also be output during the tracking NVV without a situation relevant to decision-making and/or safety being present in order, for example, to provide information about the progress of the movement of the object or to display the precision of the control with regard to the planned path.

As an alternative to an X-ray device with a C-arm, it is also possible to use other image devices (e.g., a computed tomography unit or a magnetic resonance scanner).

The present embodiments may be briefly summarized as follows: for improved patient safety, a method is provided for automatically monitoring a robot-assisted movement of a medical object through a hollow organ of a patient performed by a robotic system. The method includes tracking the movement of the medical object by a medical imaging device such that the medical object and/or the hollow organ are at least partially arranged in the recording region that may be mapped by the imaging device. The tracking is effected by a relative movement between the recording system of the imaging device and the patient. At least one image of the recording region is recorded during the tracking. In each case, a further image is recorded at regular intervals. The current image in each case and/or sensor data from a sensor assigned to the robotic system or the object is evaluated to determine whether a situation relevant to decision-making and/or safety with respect to the robotic system is present. Information is output if the evaluation reveals a presence of a situation relevant to decision-making and/or safety.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically monitoring a movement of a medical object through a hollow organ of a patient performed by a robotic system, such that the movement is robot-assisted, the method comprising:

tracking, by a medical imaging device, the movement of the medical object, such that the medical object, the hollow organ, or the medical object and the hollow organ are at least partially arranged in a recording region that is mappable by the imaging device, wherein the tracking is effected by a relative movement between a recording system of the imaging device and the patient;

recording, by the recording system of the imaging device, at least one image of the recording region during the tracking, wherein in each case a further image is recorded at regular intervals;

evaluating a current image in each case, or the current image in each case and sensor data from a sensor assigned to the robotic system or the object, such that whether a situation relevant to decision-making, safety, or decision-making and safety with respect to the robotic system is present is determined;

outputting information when the evaluating reveals the presence of the situation relevant to decision-making, safety, or decision-making and safety; and displaying the current image, the evaluation of which reveals the presence of the situation relevant to decision-making, safety, or decision-making and safety, such that the displaying of the current image, the evaluation of which reveals the presence of the situation relative to decision-making, safety, or decision-making and safety, is held until acceptance of a user input or until receipt of a control command for resuming the movement that is robot-assisted, the image recording, or the movement and the image recording, the current image being recorded at a same point in time as the sensor data that reveals the presence of the situation relevant to decision-making, safety, or decision-making and safety, wherein a control signal for interrupting the movement that is robot-assisted, the image recording, or the movement and the image recording is automatically output when the evaluating reveals the presence of the situation relevant to decision-making, safety, or decision-making and safety, and wherein the situation relevant to decision-making, safety, or decision-making and safety is present when a branch or a bifurcation of the hollow organ is detected during the evaluation or when a deviation from existing path planning exceeds a threshold value.

2. The method of claim 1, wherein the tracking is at least partially based on control signals from the robotic system.

3. The method of claim 2, wherein a control signal for interrupting the movement that is robot-assisted, the image recording, or the movement and the image recording is automatically output when the evaluating reveals the presence of the situation relevant to decision-making, safety, or decision-making and safety, and wherein the method further comprises displaying the information.

4. The method of claim 1, wherein path planning for an automatic or semi-automatic movement of the medical object is provided.

5. A medical system comprising:
a robotic system comprising:
a robot control unit; and
a robot-assisted drive system comprising a drive and a drive mechanism, wherein the robot-assisted drive system is configured to move a medical object in a cavity organ of a patient based on control signals from the robot control unit;
a system control unit;
a movable imaging device configured to record images of a mappable recording region, wherein the system control unit is configured to actuate the movable imaging device, such that movement of the medical object is tracked;
a processor configured to evaluate images of the movable imaging device, such that whether a situation relevant to decision-making, safety, or decision-making and safety with respect to the robotic system is present is determined;
a display unit configured to output information, the output of the information comprising display of a current image, the evaluation of which reveals the presence of the situation relevant to decision-making, safety, or decision-making and safety, such that the display of the current image, the evaluation of which reveals the presence of the situation relevant to decision-making, safety, or decision-making and safety, is held until acceptance of a user input or until receipt of a control command for resumption of the movement that is robot-assisted, the image recordation, or the movement and the image recordation, the current image being recorded at a same point in time as the sensor data that reveals the presence of the situation relevant to decision-making, safety, or decision-making and safety,
wherein a control signal for interruption of the movement that is robot-assisted, the image recordation, or the movement and the image recordation is automatically output when the evaluation reveals the presence of the situation relevant to decision-making, safety, or decision-making and safety, and
wherein the situation relevant to decision-making, safety, or decision-making and safety is present when a branch or a bifurcation of the hollow organ is detected during the evaluation or when a deviation from existing path planning exceeds a threshold value.

6. The medical system of claim 5, further comprising an input configured to actuate the robotic system.

7. The medical system of claim 6, wherein the robot control unit and the system control unit are configured to exchange data.

8. The medical system of claim 7, further comprising a patient table, the patient table having a table top,
wherein the patient table, the table top, or the patient table and the table top are actuatable, such that a movement relative to the movable imaging device is executed.

9. The medical system of claim 6, wherein the input comprises a joystick, a touchpad, or a rotary regulator.

10. The medical system of claim 5, wherein the robot control unit and the system control unit are configured to exchange data.

11. The medical system of claim 5, further comprising a patient table, the patient table having a table top,
wherein the patient table, the table top, or the patient table and the table top are actuatable, such that a movement relative to the movable imaging device is executed.

12. The medical system of claim 5, further comprising a position-determining system, the position-determining system comprising at least one sensor, the at least one sensor being arranged on or assigned to the robotic system or the object, wherein the position-determining system is configured to determine a position of the object.

13. The medical system of claim 5, wherein the movable imaging device is a movable X-ray device.

* * * * *